US012582581B2

(12) United States Patent
Ueda et al.

(10) Patent No.: US 12,582,581 B2
(45) Date of Patent: Mar. 24, 2026

(54) LAMINATE SHEET FOR COSMETIC, AND COSMETIC SET

(71) Applicant: PANASONIC INTELLECTUAL PROPERTY MANAGEMENT CO., LTD., Osaka (JP)

(72) Inventors: Mari Ueda, Osaka (JP); Masato Minami, Hyogo (JP); Yuto Enomoto, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 376 days.

(21) Appl. No.: 18/126,089

(22) Filed: Mar. 24, 2023

(65) Prior Publication Data

US 2023/0277420 A1 Sep. 7, 2023

Related U.S. Application Data

(63) Continuation of application No. PCT/JP2021/043019, filed on Nov. 24, 2021.

(30) Foreign Application Priority Data

Dec. 4, 2020 (JP) ................................. 2020-201598

(51) Int. Cl.
| | |
|---|---|
| *A61K 8/02* | (2006.01) |
| *A45D 44/00* | (2006.01) |
| *A61Q 1/00* | (2006.01) |

(52) U.S. Cl.
CPC ............ *A61K 8/0233* (2013.01); *A45D 44/00* (2013.01); *A61Q 1/00* (2013.01); *A61K 2800/87* (2013.01); *A61K 2800/88* (2013.01)

(58) Field of Classification Search
CPC .............. A61K 8/0233; A61K 2800/87; A61K 2800/88; A45D 44/00; A61Q 1/00
See application file for complete search history.

(56) References Cited

U.S. PATENT DOCUMENTS

| | | | | |
|---|---|---|---|---|
| 9,585,461 | B2 * | 3/2017 | Kusukame ........... | A45D 44/002 |
| 2002/0155234 | A1 | 10/2002 | Seth | |

| | | | | |
|---|---|---|---|---|
| 2003/0091617 | A1 | 5/2003 | Mrozinski et al. | |
| 2003/0211954 | A1 | 11/2003 | Kono et al. | |
| 2014/0318565 | A1 * | 10/2014 | Ito ........................... | A45D 44/22 |
| | | | | 132/319 |
| 2018/0207066 | A1 * | 7/2018 | Lechanoine ........... | A45D 33/34 |
| 2019/0200726 | A1 | 7/2019 | Shinoda et al. | |

FOREIGN PATENT DOCUMENTS

| | | | |
|---|---|---|---|
| CN | 1436055 | | 8/2003 |
| EP | 3 949 801 | | 2/2022 |
| JP | 2002-87956 | | 3/2002 |
| JP | 2007-204393 | | 8/2007 |
| JP | 2012-12711 | | 1/2012 |
| JP | 2012000295 | A * | 1/2012 |
| JP | 2012012711 | A * | 1/2012 |
| JP | 2015-43836 | | 3/2015 |
| JP | 2016-215506 | | 12/2016 |
| KR | 10-0911753 | | 8/2009 |
| WO | 01/97669 | | 12/2001 |
| WO | 2018/061486 | | 4/2018 |
| WO | 2020/202740 | | 10/2020 |

OTHER PUBLICATIONS

Leda Coltro and Joyce Borghetti. "Plastic Packages for Personal Care Products—Evaluation of Light Barrier Properties," Polímeros: Ciência e Tecnologia, 2007, vol. 17, No. 1, p. 56-61. (Year: 2007).*
JP 2010/000295 A; English translation provided by Google Patents (Year: 2025).*
JP-2012012711-A; English machine translation from EPO (Year: 2025).*
Extended European Search Report issued in EP Application No. 21900470.2, dated Nov. 9, 2023.
International Search Report issued in International Patent Application No. PCT/JP2021/043019, dated Jan. 18, 2022.

* cited by examiner

*Primary Examiner* — Michael P Cohen

(74) *Attorney, Agent, or Firm* — GREENBLUM & BERNSTEIN, P.L.C.

(57) ABSTRACT

An aspect of the present invention relates to a cosmetic laminate sheet including a porous film having micropores and a thin film sheet superposed on the porous film, the porous film having a porosity of 35% or more and 55% or less.

14 Claims, 4 Drawing Sheets

LAMINATE SHEET FOR COSMETIC, AND COSMETIC SET

TECHNICAL FIELD

The present invention relates to a cosmetic laminate sheet and a cosmetic set.

BACKGROUND ART

In recent years, as a new method to deal with various skin problems such as blemishes, wrinkles, pores, bruises, and scars, it has been proposed to apply ink containing various coloring materials to a thin film and attach this to the human body to make blemishes, bruises, scars and the like (hereinafter also referred to as discolored regions) on the skin inconspicuous (for example, Patent Literature 1). In the technique of Patent Literature 1, an image of the skin is captured and the discolored region is identified. Then, a thin film sheet is printed in a color similar to the color around the discolored region, and this is attached to the skin to make the discolored region inconspicuous.

However, since the thin film sheet is extremely thin, it is difficult to attach the sheet to the skin without wrinkling and the like. Therefore, Patent Literature 2 proposes a method of attaching a thin film sheet to the skin using a jig. In the thin film attaching device disclosed in Patent Literature 2, a laminate obtained by laminating a support (mount) and a thin film sheet is placed on a jig so that the thin film sheet and the jig face each other, and water is sprayed on the mount side. Thereafter, the mount is peeled off, and the exposed thin film sheet is brought into close contact with the skin, and then the jig is peeled off from the thin film sheet.

In the thin film attaching device described in Patent Literature 2 above, the thin film sheet and the jig (hydrophilic sheet) are housed separately, for example, in the form of a compact or the like, the thin film sheet is used by being temporarily pasted to the surface of the jig when attached to the skin. However, in such an embodiment, a mount (support) is essential for storage of the thin film sheet, but there has been a drawback that the thin film sheet adheres to this mount and this makes it difficult to mount the thin film sheet on the jig. In addition, since there are many operations that should be performed by the user, the thin film sheet is prone to wrinkling during a series of investigations, and there have been cases where it is not possible to attach the thin film sheet to the skin well. Furthermore, when water is sprayed on the thin film sheet through the mount, the thin film sheet moves on the jig in some cases, and there are still problems in terms of handling.

The present invention is made in view of such circumstances, and a main object thereof is to provide a cosmetic laminate sheet, which is excellent in handleability and can be accurately attached to a desired adherend by a relatively easy operation by a user.

CITATION LIST

Patent Literatures

Patent Literature 1: JP 2015-43836 A
Patent Literature 2: WO 2018/061486 A

SUMMARY OF INVENTION

As a result of intensive studies, the present inventors found out that the problems can be solved by a cosmetic laminate sheet having the following configuration, and completed the present invention by conducting further studies based on this finding.

In other words, a cosmetic laminate sheet relating to an aspect of the present invention includes a porous film having micropores and a thin film sheet superposed on the porous film, in which the porous film has a porosity of 35% or more and 55% or less.

DESCRIPTION OF EMBODIMENTS

Hereinafter, embodiments according to the present invention will be specifically described, but the present invention is not limited thereto.
(Laminate Sheet for Cosmetic)

As described above, the cosmetic laminate sheet of the present embodiment includes at least a porous film having micropores and a thin film sheet superposed on the porous film, and the porosity of the porous film in the porous film is 35% or more and 55% or less.

According to such a configuration, it is possible to provide a cosmetic laminate sheet that is easily operated until to be attached to the skin and can be accurately attached to a desired adherend, and a cosmetic set including the same.

By forming a laminate sheet in which a porous film (jig) and a thin film sheet are laminated in advance as described above, the mount (support), which used to be required for holding and storing the thin film sheet in the conventional technique, is no longer necessary, and the procedure for peeling off this mount from the thin film sheet can be eliminated.

The porous film of the present embodiment acts as a jig, and by using a porous film in this way, the holes play a role of anti-slip, and there is an advantage that the thin film sheet laminated in advance is less likely to shift during the attaching operation. When the thin film sheet is attached to the skin, the thin film sheet is easily transferred to the skin since the contact area between the thin film sheet and the porous film is smaller than that between the thin film sheet and the skin.

Figure 1:
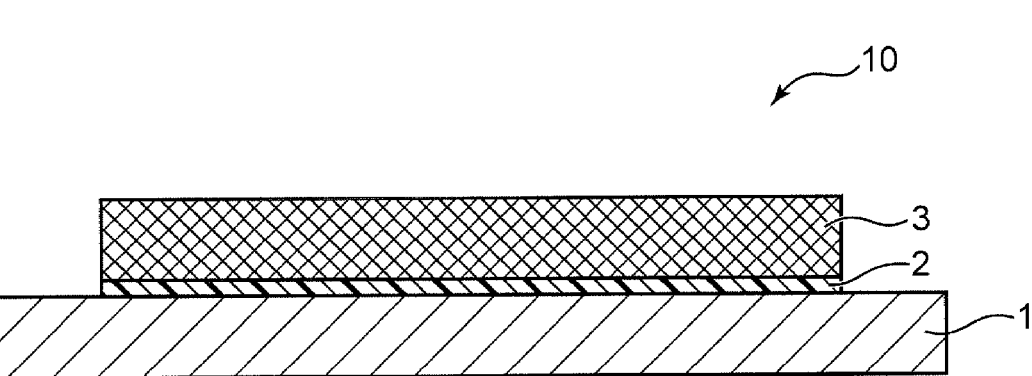
FIG. 1 is a schematic sectional view illustrating the configuration of a cosmetic laminate sheet according to an embodiment of the present invention.

The cosmetic laminate sheet of the present embodiment (hereinafter also simply referred to as "laminate sheet")

includes at least a porous film and a thin film sheet as described above, but may further include a covering sheet on the thin film sheet for the purpose of protecting the thin film sheet. In this case, the lamination order of a cosmetic laminate sheet 10 is the order of a porous film 1, a thin film sheet 2, and a covering sheet 3 as illustrated in FIG. 1. In the following description of the drawings, the respective reference signs denote: 1 porous film, 2 thin film sheet, 3 covering sheet, 10 cosmetic laminate sheet, 21 thin film, 22 colored layer or light scattering layer.

The cosmetic laminate sheet of the present embodiment may be a single sheet as illustrated in FIG. 1, but can also be a tear-off patch type sheet in which a plurality of thin film sheets are laminated on the porous film 1 and perforations are provided at positions surrounding each thin film sheet.

Each component of the laminate sheet will be described in more detail.

(Porous Film)

The laminate sheet 10 of the present embodiment includes the porous film 1 having micropores, and this porous film 1 is disposed on one surface of the thin film sheet 2 and can be used as a jig or the like when the thin film sheet 2 is attached.

By using the porous film 1, the contact area with the thin film sheet 2 decreases by micropores of the porous film 1, and the degree of close contact with the thin film sheet 2 is thus diminished. Since the aqueous liquid enters micropores of the porous film 1, the width of the aqueous liquid layer between the porous film 1 and the thin film sheet 2 increases. Therefore, the thin film sheet 2 is likely to be peeled off from the porous film 1 (jig), and the thin film sheet 2 is easily transferred to the adherend.

In the porous film of the present embodiment, the "micropores" may be through holes or non-through holes as long as the contact area with the thin film sheet can be decreased. The shape of the micropores of the present embodiment may be circular, elliptical, polygonal (including honeycomb structure), or the like, but is preferably circular from the viewpoint that the thin film sheet is not caught in the micropores when the thin film sheet on the jig is transferred from the jig to the skin. When the thin film sheet is caught in the micropores, the thin film sheet may be torn or scratched, and the thin film sheet may be unlikely to be transferred to the skin side. The diameter D of the micropores (average value of diameters of the micropores) of the present embodiment is preferably 0.6 mm or more and 2.6 mm or less, still more preferably 0.6 mm or more and 2 mm or less.

The porosity of the porous film (proportion of micropores in the porous film) of the present embodiment is 35% or more and 55% or less.

In the present embodiment, the porosity A means a value determined by the following Equation (1).

$$A = 78.5 \times D^2 / P^2 \tag{1}$$

Figure 2:
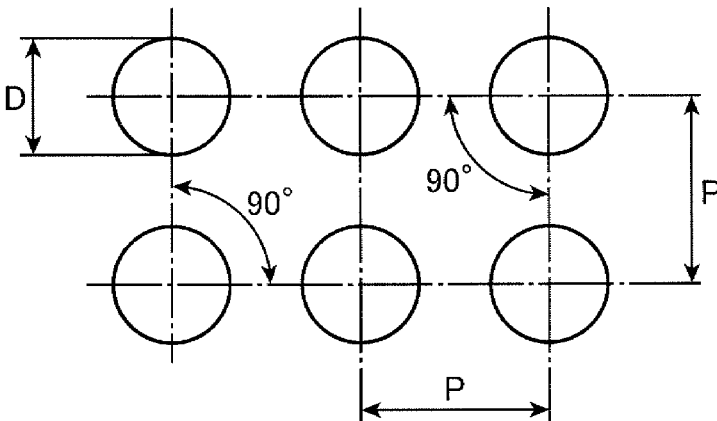
FIG. 2 is a schematic view illustrating an example of micropores in a porous film equipped in a cosmetic laminate sheet.

In Equation (1), D denotes the diameter of micropores as illustrated in FIG. 2, and P denotes the pitch between micropores as illustrated in FIG. 2. The pore diameter refers to the average value of diameters of micropores.

FIG. 2 illustrates a case where the pitches between micropores are evenly spaced, but the P is determined as the average value of pitches between micropores in a case where the pitches are not evenly spaced.

When the porosity is within the range described above, the thin film sheet can be easily attached to the skin. It is difficult to acquire the effects described above when the porosity is less than 35%, and the thin film sheet laminated on the porous film has poor durability and is likely to tear when the porosity exceeds 55%.

The porous film of the present embodiment is preferably hydrophilic. In the present embodiment, being hydrophilic means that the contact angle of the porous film with water is 90° or less. A more preferable contact angle is 50° or less. As the porous film is hydrophilic, a water-soluble layer is easily formed on the surface of the porous film, and the thin film sheet is easily brought into close contact.

The contact angle with water herein can be a value measured by the θ/2 method or by determining the angle of the straight line connecting the left and right end points and the apex of a droplet with respect to the solid surface and doubling this.

Since the porous film is equipped to prevent the thin film sheet from bending when the thin film sheet is attached to the adherend, it is preferable that the porous film has a structure excellent in flexibility, and is elastically deformed according to the unevenness of the adherend when the thin film sheet is pressed against the adherend. Hence, the Asker C hardness of the porous film is preferably 4 degrees or more and 20 degrees or less. The Asker C hardness herein can be a value measured using an Asker C hardness tester.

From the viewpoint of being preferable that the porous film can be elastically deformed as above, the elastic modulus of the porous film is preferably 100 MPa or more and 100,000 MPa or less. The elastic modulus in the present specification can be a value measured using an elastic modulus measuring device based on a static test method (bending test), a transverse vibration method, a cantilever resonance method, or an ultrasonic method (pulse echo overlap method).

The shape of the porous film of the present embodiment is appropriately selected according to the shape of the adherend, the shape of the thin film sheet, and the like, and may be flat or may have a curved surface (concave or convex). The thickness of the porous film is not particularly limited, and is preferably about 1 μm to 10 mm, still more preferably about 50 μm to 8 mm from the viewpoint of handleability.

The porous film preferably has an area larger than that of the thin film sheet in order to remove the porous film after the thin film sheet is attached to the adherend. In other words, it is preferable that the porous film has a portion where the thin film sheet is not laminated. It becomes easier to remove the porous film (jig) by using this portion as a gripping margin.

Figures 3A, 3B, 3C, 3D:
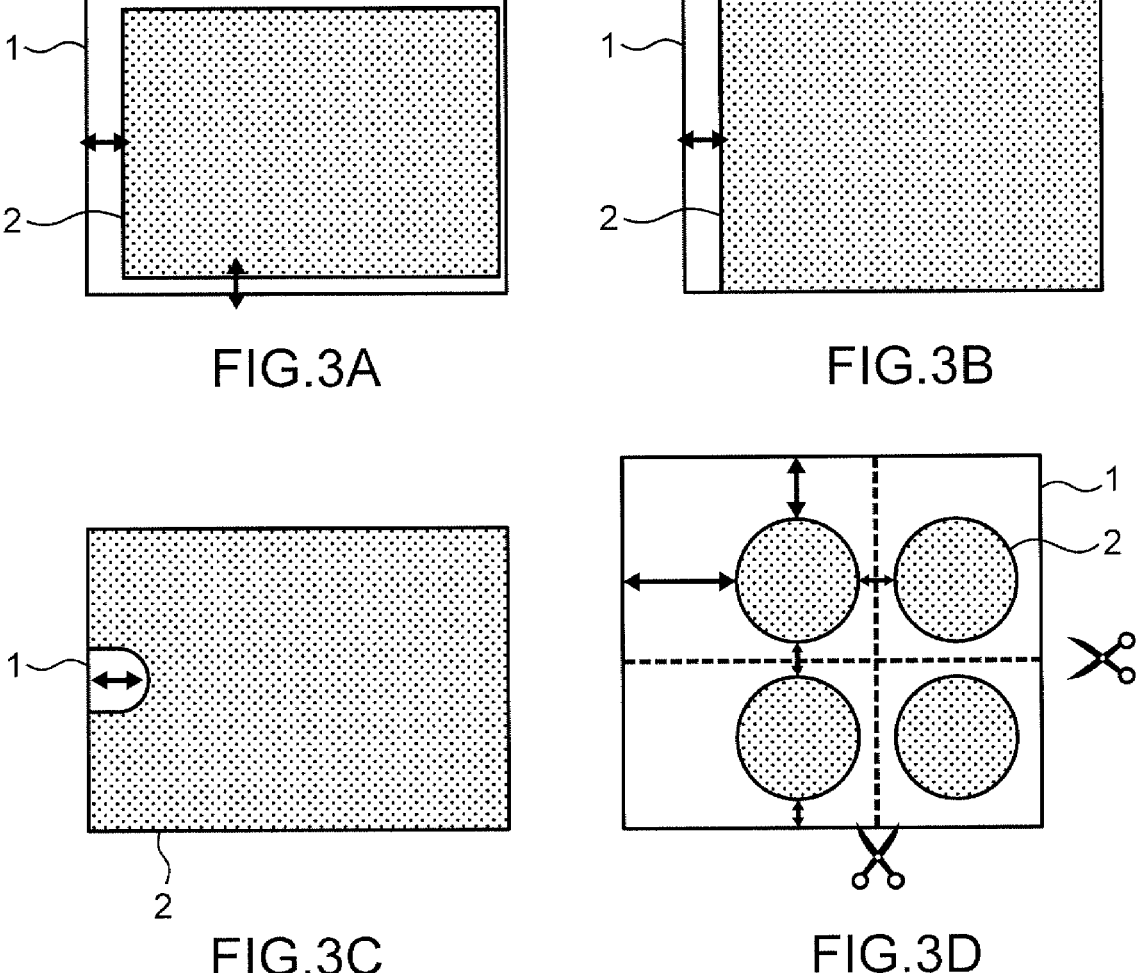
FIG. 3A is a top view of a cosmetic laminate sheet according to an embodiment of the present invention viewed from the thin film sheet side.
FIG. 3B is a top view of a cosmetic laminate sheet according to another embodiment of the present invention viewed from the thin film sheet side.
FIG. 3C is a top view of a cosmetic laminate sheet according to a further embodiment of the present invention viewed from the thin film sheet side.
FIG. 3D is a top view of a cosmetic laminate sheet according to a yet another embodiment of the present invention viewed from the thin film sheet side.

Specifically, for example, a shape as illustrated in FIG. 3 may be mentioned. The size of the portion where the thin film sheet is not laminated of the porous film is not particularly limited, but the shortest distance among the distances from the end of the porous film to the thin film sheet is preferably 3 mm or more in the cases of (A) to (C) in FIG. 3, for example, from the viewpoint of ease of removal of the porous film. The example illustrated in FIG. 3(D) shows a case where the cosmetic laminate sheet is of a tear-off patch type, and in such an embodiment, it is preferable that the shortest distance among the distances from the end of the porous film to the thin film sheet or the pitches between a plurality of thin film sheets is 3 mm or more.

The porous film may be formed of one layer (single layer film) or may be formed of two or more layers (multilayer film). For example, the porous film may be configured by laminating a hydrophilic film and a substrate exhibiting desired elasticity. These may be bonded together with an adhesive or the like. When the porous film is a laminate of a hydrophilic film and an elastic substrate, even if the surface (adherend) to which the thin film sheet is attached is curved or the like, the porous film can follow the shape and it is easy to bring the thin film sheet into close contact with the adherend. The surface of the porous film facing the thin film sheet may be smooth or uneven.

The porous film of the present embodiment may or may not be transparent. However, the porous film is preferably transparent from the viewpoint that the attaching position of the thin film sheet is easily visually recognized when the thin film sheet is attached to the adherend. In the present embodiment, "being transparent" means, for example, having a light transmittance of 40% or more at a wavelength of 550 mm. The transmittance can be a value measured using a transmittance measuring device ("Ultraviolet/visible/near-infrared spectrophotometer (UV-3600Plus)" manufactured by Shimadzu Corporation).

Furthermore, the porous film may be provided with a structure (for example, a screw thread provided on the side surface) for being joined with a container, a protective member, and the like when a cosmetic set described later is configured, a convex portion or a concave portion for positioning therewith, and the like. A perforation may be formed at a position surrounding the thin film sheet so that the thin film sheet is easily taken out from the cosmetic set.

The porous film of the present embodiment is not particularly limited as long as it is configured to exhibit above-described properties, but is preferably a hydrophilic film exhibiting low water absorbing properties.

As used herein, the term "film exhibiting low water absorbing properties" means a film that hardly retains water or aqueous liquids in the internal structure thereof. When the water absorbing properties are low, the peelability of the thin film sheet from the porous film is favorable. From the viewpoint of antiseptic properties as well, the porous film can be kept hygienic by reducing the risk of bacterial growth.

As used herein, the term "hydrophilic film" refers to a film having a contact angle with water of 90° or less as described above, but this means a film, which exhibits high affinity for water or aqueous liquids on the surface thereof (the interface between the film and the air layer) and in which the water or aqueous liquids easily spread over the surface. When the porous film is such a hydrophilic film, water (liquid) is likely to spread on the porous film of the present embodiment, the entire thin film sheet is likely to be wetted when the thin film sheet is attached, and the attaching operability is favorable. As the thin film sheet is more favorably wetted, the support is more likely to be peeled off from the thin film sheet on the porous film, and the thin film sheet is more likely to be transferred from the porous film to the skin side at the time of attachment.

A hydrophilic film exhibiting low water absorbing properties as described above has an advantage that water or an aqueous liquid does not permeate into the inside of the film as well as the water or aqueous liquid is likely to spread on the surface of the film but is less likely to be repelled when the water or aqueous liquid is dropped on the surface.

As specific examples of such a film, for example, films containing rayon, polyester, aramid, glass fibers, nylon, vinylon, polyolefins (polyethylene, polypropylene, low-density polyethylene, and the like), ethylene vinyl acetate resin, synthetic rubber, copolyamide resin, copolyester resin and the like, a silicon (Si)-based film containing a hydrophilic agent, an elastomer film containing a hydrophilic agent, and rubber-based films composed of an aqueous gel and the like can be used as the porous film. These films may be films subjected to various hydrophilization treatments.

Among these films, it is particularly preferable to use films containing polyester, aramid, glass fibers, nylon, polyolefins (polyethylene, polypropylene, low-density polyethylene, and the like), ethylene vinyl acetate resin, synthetic rubber, copolyamide resin, or copolyester resin and the like, a silicon (Si)-based film containing a hydrophilic agent, an elastomer film containing a hydrophilic agent, and rubber-based films composed of an aqueous gel and the like.

Still more preferably, in order to obtain a hydrophilic film, it is still more preferable to use films, such as films containing polyester, polyolefins (polyethylene, polypropylene, low-density polyethylene, and the like), synthetic rubber, copolyester resin and the like, which are subjected to a hydrophilization treatment, a silicon (Si)-based film containing a hydrophilic agent, an elastomer film containing a hydrophilic agent, and rubber-based films composed of an aqueous gel and the like.

From the viewpoint of cost and workability, it is preferable to use polyester, particularly polyethylene terephthalate, which is subjected to a hydrophilization treatment, among these.

In the present embodiment, the hydrophilization treatment includes plasma treatment, UV ozone treatment, water-soluble resin coating, desensitization treatment, and the like.

(Thin Film Sheet)

The thin film sheet 2 equipped in the cosmetic laminate sheet 10 of the present embodiment may be a sheet for use by a specific person (a sheet fabricated on demand), which is fabricated according to the discolored portion of the skin of a specific individual through a known makeup support system or the like. Meanwhile, the thin film sheet 2 may be a sheet or the like that is fabricated according to the average skin color of an unspecified large number of people and is intended for use by an unspecified large number of people. The thin film sheet 2 can be used not only to color the skin, but also to make the discolored portion inconspicuous or to decorate the discolored portion by being attached to the discolored portion of the skin. Furthermore, the thin film sheet 2 may be a sheet equipped with a cosmetic ingredient layer containing cosmetic ingredients such as a moisturizing ingredient and a whitening ingredient, for purposes other than makeup (changing the skin color).

The thin film sheet 2 is a sheet with a thickness of 10 μm or less to be stuck to the skin. The thickness of the thin film sheet is preferably 10 nm to 10 μm, more preferably 10 nm to 1000 nm. When the thickness of the thin film sheet 2 is within the above range, there is an advantage that uncomfortable feeling is not caused when the thin film sheet 2 is stuck to the adherend such as the skin.

The thin film sheet of the present embodiment is preferably a biocompatible sheet-like member that does not cause uncomfortable feeling when attached to human skin. Preferably, the thin film is usually colorless and transparent or translucent. The thin film sheet is used for cosmetic purposes, and is thus preferably a sheet formed of a water-permeable thin film.

The thickness of the thin film sheet is preferably 10 nm to 10 μm, more preferably 10 nm to 1000 nm. In particular, when the thin film is hydrophobic, the thickness of the thin film is particularly preferably 10 nm to 800 nm.

The shape of the thin film sheet in plan view is not particularly limited, and is appropriately selected according to the shape of the attachment portion of the thin film sheet and the application. The thin film sheet may have cuts formed on the outer periphery and/or in the plane so as to fit the shape of the attachment portion.

The thin film sheet may be a sheet formed by a spin coating method, a roll-to-roll method, an LB method (Langmuir-Blodgett method), or the like, a fiber sheet in which fibers generated by an electrospinning method or the like are folded, or the like.

In the present embodiment, the thin film sheet is preferably hydrophilic. Being hydrophilic is synonymous with the definition described for the porous film.

The material forming the thin film sheet is not particularly limited as long as it is a material exhibiting biocompatibility, but examples thereof include polyesters represented by polyglycolic acid, polylactic acid, polycaprolactone, polyethylene succinate, polyethylene terephthalate, or copolymers thereof; polyethers represented by polyethylene glycol and polypropylene glycol; polyamides represented by nylon, polyglutamic acid, polyaspartic acid, or salts thereof; polysaccharides represented by pullulan, cellulose, starch, chitin, chitosan, alginic acid, hyaluronic acid, and cornstarch, or salts thereof; silicones represented by acrylic silicones and trimethylsiloxysilicates; acrylic acids represented by alkyl acrylates, silicone acrylates, acrylic acid amides, and copolymers thereof; polyvinyl alcohol; polyurethane; polycarbonate; polyanhydrides; polyethylene; polypropylene; porous layer coating sheets, and nanofiber sheets.

Among these, it is preferable that the material for the thin film sheet is polylactic acid, cellulose (for example, carboxymethylcellulose or hydroxyethylcellulose), starch, chitin, chitosan, alginic acid, corn starch, or polyurethane since there are advantages such as biocompatibility, easy availability, and favorable handleability.

Preferably, it is preferable to use a film of polylactic acid, cellulose (for example, carboxymethylcellulose or hydroxyethylcellulose), starch, chitin, chitosan, or the like in order to form the thin film sheet as a hydrophilic film.

The thin film sheet preferably has at least one layer among a colored layer, a light scattering layer, and a layer containing a cosmetic ingredient on the surface of the porous film side. In particular, when the thin film sheet has a colored layer, a light scattering layer and the like in addition to the thin film, it is possible to color the adherend (for example, skin) in an arbitrary color by attaching the thin film sheet. More specifically, it is possible to color the skin or make the discolored portion of the skin look normal color. When the thin film sheet has a colored layer and the like, it is preferable to attach the thin film sheet so that the thin film in the thin film sheet is in contact with the adherend. When the adherend is the skin of a human body, the skin is less likely to be irritated by attaching the thin film sheet so that a biocompatible thin film is in contact with the skin. Therefore, when the thin film sheet has a colored layer, lamination is performed so that the side on which the colored layer or the like of the thin film is formed is in contact with the porous film and the colored layer or the like is in contact with the covering sheet described later.

The colored layer disposed on the thin film sheet contains a coloring material and a binder. The colored layer may further contain a film forming agent, a dispersant, various additives, and the like. The color of the colored layer can usually be a color that matches the skin, but can be an arbitrary color in the case of using the thin film sheet as a cosmetic such as blush, eye shadow or body painting. The entire thin film sheet may be the same color, or a regions with different colors may be disposed at a part of the thin film sheet.

The colored layer may be formed of one layer or two or more layers. When the colored layer is formed of a plurality of layers, the kinds of coloring materials contained in the respective layers may be the same as or different from each other. The amounts of coloring materials contained in the respective layers may be the same as or different from each other. For example, the colored layer may have a configuration in which a colored layer in an arbitrary color is laminated on a colored layer with the skin color.

Examples of coloring materials contained in the colored layer include inorganic red pigments such as iron oxide and iron titanate such as iron hydroxide; inorganic brown pigments such as $\gamma$-iron oxide; inorganic yellow pigments such as yellow iron oxide and ocher; inorganic black pigments such as black iron oxide and carbon black; inorganic violet pigments such as manganese violet and cobalt violet; inorganic green pigments such as chromium hydroxide, chromium oxide, cobalt oxide, and cobalt titanate; inorganic blue pigments such as iron blue (ferric ferrocyanide), ultramarine blue, lapis lazuli, mountain blue, aluminum-cobalt oxide, aluminum-zinc-cobalt oxide, silicon-cobalt oxide, silicon-zinc-cobalt oxide, cobalt pigment, smalt, cobalt blue, cobalt stannate, cobalt chromium blue, cobalt-aluminum-silicon oxide, and manganese blue; organic blue pigments or dyes such as indigo, phthalocyanine, indanthrene blue, and sulfonates thereof; lakes of various tar-based colourants, lakes of various natural colourants, and synthetic resin powders obtained by compounding these powders.

Meanwhile, the shape of the binder contained in the colored layer is not particularly limited, but is preferably particulate, and the binder is preferably particles particularly formed of (meth)acrylic resin (hereinafter also simply referred to as "acrylic particles"). When the binder is formed of acrylic particles, the fixability of the above-described coloring material is likely to be favorable, and the durability of the colored layer is likely to be favorable. The binder is still more preferably particles formed of a (meth)acrylic resin that does not irritate the skin. Therefore, the acrylic particles are preferably selected from ingredients listed in the list of cosmetic ingredient display names based on the Pharmaceutical Affairs Law of Japan, ingredients that comply with the EU Cosmetics Directive (Cosmetics Directive 76/768/EEC), ingredients listed in the International Cosmetic Ingredient Dictionary and Handbook (Jan. 1, 2002, 9th edition) by the US CTFA (Cosmetic, Toiletry & Fragrance Association, U.S.), and the like, and the acrylic particles are preferably acrylic resin particles that are applied to known cosmetics and the like.

The amount of the binder contained in the colored layer is preferably 0.5 to 10 parts by mass, more preferably 1.5 to 5.7 parts by mass when the amount of the coloring material is 10 parts by mass. When the amount of the binder with respect to the amount of the coloring material is within the above range, the fixability of the coloring material is enhanced. When the amount of the binder is within the above range, the amount of the coloring material is likely to be relatively sufficient, and the desired color of the colored layer can be obtained.

The thickness of the colored layer is appropriately selected according to the desired color depth and the like, but is preferably 10 nm to 15 μm, more preferably 10 nm to 3 μm. When the thickness of the colored layer is within this range, desired color development is likely to be obtained without causing a feeling of thick coating. When a plurality of colored layers are laminated, the total thickness of these layers is preferably within this range.

Such a colored layer can be formed by applying an ink containing a coloring material and a binder onto the surface of the thin film by, for example, inkjet printing, screen printing, offset printing, or gravure printing. The ink may be oil-based ink or water-based ink. Among these, the inkjet method is preferable from the viewpoint that it is easy to perform on-demand printing or it is possible to perform lamination printing in which cosmetic ink is applied multiple times.

Meanwhile, the light scattering layer contains a reflective material and a binder. The light scattering layer may further contain a film forming agent, a dispersant, various additives, and the like. The light scattering layer may be formed of one layer or two or more layers. When the light scattering layer is formed of a plurality of layers, the kinds of reflective materials contained in the respective layers may be the same as or different from each other. The amounts of reflective materials contained in the respective layers may be the same as or different from each other.

The reflective material contained in the light scattering layer may be particles that scatter or reflect ultraviolet light and visible light (for example, light having a wavelength of 200 to 780 nm), and can be, for example, a pearlizing agent, a soft focus agent, or a lame agent. It is preferable that the pearlizing agent, soft focus agent and lame agent do not irritate the skin.

The amount of the binder contained in the light scattering layer is preferably 0.5 to 10 parts by mass, more preferably 1.5 to 5.7 parts by mass when the amount of the reflective material is 10 parts by mass. When the amount of the binder with respect to the amount of the reflective material is within the above range, the fixability of the reflective material is enhanced. When the amount of the binder is within this range, the amount of the reflective material is likely to be relatively sufficient, and the light scattering layer can sufficiently reflect or scatter light.

The thickness of the light scattering layer is preferably 10 nm to 120 μm, more preferably 10 nm to 100 μm. When the thickness of the light scattering layer is within this range, the light reflected from the surface of the skin is likely to be sufficiently reflected from the light scattering layer.

The thin film sheet of the present embodiment may be provided with a layer containing cosmetic ingredients such as a whitening ingredient and a moisturizing ingredient, in addition to the colored layer and the light scattering layer. As the whitening ingredient and moisturizing ingredient in that case, known whitening ingredients and moisturizing ingredients can be used without particular limitations. Specifically, moisturizing ingredients such as fatty acids and fatty alcohols; whitening ingredients such as vitamin C; and vitamin E, hyaluronic acid and collagen may be mentioned as the cosmetic ingredients. The cosmetic ingredients may be contained in the liquid that forms the layer containing cosmetic ingredients at 1% to 100% by mass, more preferably 1% to 50% by mass.

The liquid may contain a solvent, and any solvent that hardly irritates the skin (or does not irritate the skin) can be used without particular limitation. The amount of the solvent in the liquid may be appropriately set according to the desired viscosity of the liquid, and is, for example, 99% by mass or less, preferably 50% to 99% by mass.

A surfactant and the like that are approved as cosmetic ingredients can be further added to the liquid.

Furthermore, in the thin film sheet, a gloss layer, a hygroscopic layer and the like may be further laminated as long as the objects and effects of the present embodiment are not impaired. When the hygroscopic layer is disposed, the humidity on the surface side of the thin film sheet is controlled and comfortability is enhanced. The hygroscopic layer usually contains a hygroscopic agent, and examples of the hygroscopic agent include spherical silica, porous acrylic particles, and nylon 6 (polyamide 6).

(Covering Sheet)

The cosmetic laminate sheet of the present embodiment may further include a covering sheet. The covering sheet is equipped to protect the thin film sheet, and is a sheet that is placed on the thin film sheet only for the purpose of protection, unlike a mount (support) equipped in a conventional thin film sheet for cosmetic. In other words, conventionally, the mount and the thin film sheet are laminated and integrated, but the covering sheet and the thin film sheet are not in close contact (integrated) in the present embodiment.

The shape of the covering sheet may be the same as the shape of the thin film sheet described above, or may be a larger shape than that of the thin film sheet. For example, the covering sheet may have a gripping margin or the like for gripping when the covering sheet is removed from the thin film sheet in attaching.

The covering sheet is preferably formed of a hydrophilic material, and examples thereof include sheets formed of non-woven fabrics, paper, woven fabrics (cloths), knitted fabrics, tufts, fulled felt, porous layer coating sheets, nanofiber sheets, water absorbing polymers, water-soluble polymers, and the like. Among these, it is preferable to use sheets formed of nonwoven fabrics, paper, woven fabrics (cloths), porous layer coating sheets, nanofiber sheets, water absorbing polymers, and water-soluble polymers from the viewpoint that the material is less likely to adhere to the thin film sheet and has a smooth surface that is less likely to damage the thin film sheet.

The thickness of the covering sheet is not particularly limited, but is preferably about 1 μm to 5 mm, more preferably about 1 μm to 1 mm. When the covering sheet has such a thickness, there are advantages that the covering sheet is excellent in flexibility, stress is less likely to be applied to the thin film sheet, and the thin film sheet is less likely to be damaged.

Furthermore, one surface of the covering sheet may be colored or may have letters or patterns in order to distinguish the surface on which the thin film sheet is placed from the surface on which thin film sheet is not placed.

(Method for Fabricating Cosmetic Laminate Sheet)

The method for fabricating a cosmetic laminate sheet of the present embodiment is not particularly limited, but includes a step of preparing a thin film sheet (hereinafter also referred to as a "thin film sheet preparation step"), and a step of preparing the porous film described above and laminating the porous film so as to face the previously fabricated thin film sheet (hereinafter, also referred to as "porous film lamination step"). However, the method for fabricating a cosmetic laminate sheet of the present embodiment may include other steps if necessary.

In the thin film sheet preparation step, the thin film sheet is prepared, but the means for forming the colored layer, the light scattering layer and the like in the thin film sheet is not particularly limited, but the formation can be performed by, for example, inkjet printing, screen printing, offset printing, or gravure printing as described above.

In the porous film lamination step, the above-described porous film is first prepared, and the thin film sheet and the porous film are superimposed one on another so that the porous film faces the thin film sheet prepared in the thin film sheet preparation step described above. It is not necessary to provide an adhesive layer or the like between these, and the surface of the thin film sheet on which the colored layer or the light scattering layer is formed and the porous film are laminated together.

(Method for Attaching Cosmetic Laminate Sheet)

Next, a method for attaching the thin film sheet equipped in the cosmetic laminate sheet to the adherend will be described with reference to FIGS. 4A to 4C.

Figure 4A:
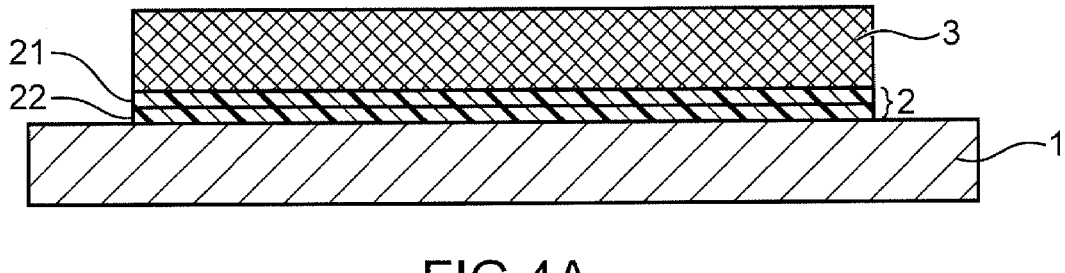
FIGS. 4A, 4B, and 4C are schematic sectional views illustrating a method of placing a cosmetic laminate sheet according to an embodiment of the present invention on an adherend.
Figure 4B:
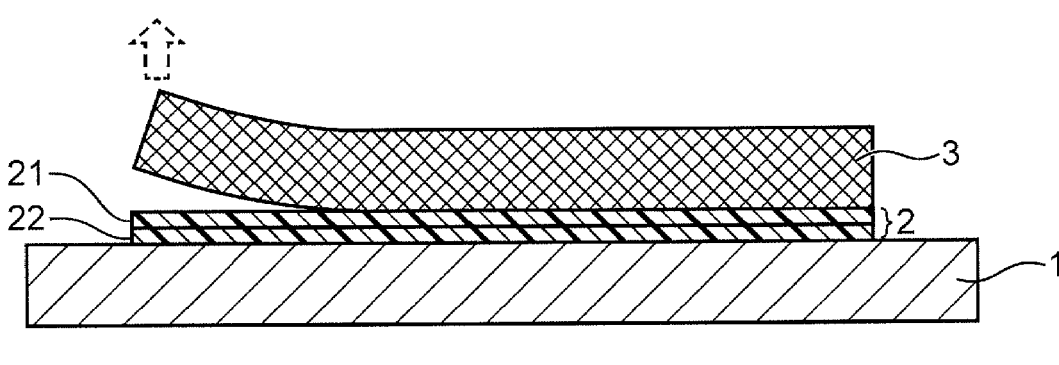
Figure 4C:
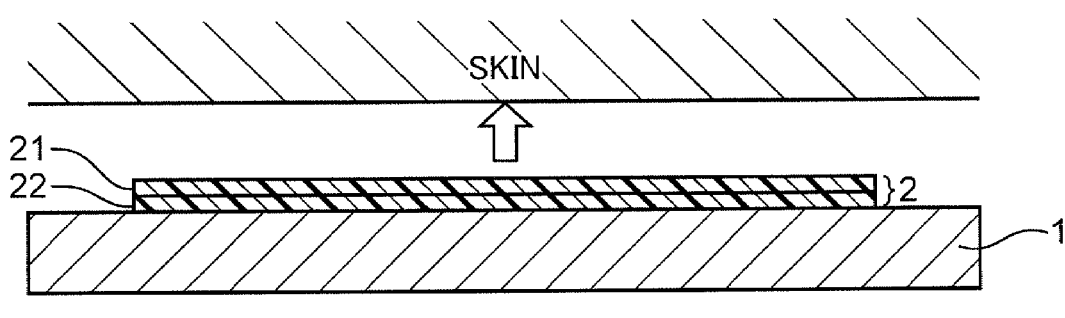

FIGS. 4A to 4C are sectional views of an embodiment of the cosmetic laminate sheet of the present embodiment. However, the method of using the laminate sheet of the present embodiment is not limited to the following method.

First, an aqueous liquid with high biological safety such as water, milky lotion, or moisturizing agent is sprayed on the entire laminate sheet in which a porous film 1, a thin film sheet 2 (formed of a thin film 21 and a colored layer or light scattering layer 22), and a protective covering sheet 3 are laminated as illustrated in FIG. 4A from the covering sheet side using a sprayer or the like. The aqueous liquid thus permeates the thin film sheet 2 and the porous film 1. Alternatively, the aqueous liquid can also permeate the thin film sheet 2 and the porous film 1 by immersing the laminate sheet in a container containing the aqueous liquid in addition to spraying as described above. Since the laminate sheet of the present embodiment is in a dry state until the aqueous liquid permeates, the laminate sheet of the present embodiment exhibits higher handleability than conventional laminate sheets for cosmetic, and also has the advantage of being prevented from deteriorating (being hydrolyzed or the like) by humidification of the thin film sheet.

After that, as illustrated in FIG. 4B, the user lifts the covering sheet 3 and peels off the covering sheet 3 from the thin film sheet 2.

Next, as illustrated in FIG. 4C, the user grips the porous film 1 and brings the thin film sheet 2 laminated on the porous film 1 into close contact with the adherend (skin). The user then presses the thin film sheet 2 against the adherend using the porous film 1 to transfer the thin film sheet 2 to the adherend. At this time, by elastically deforming the porous film 1 according to the unevenness of the adherend, the user can uniformly apply pressure to the adherend and can uniformly bring the thin film sheet 2 into close contact with the adherend.

In a case where the thin film sheet 2 is transferred to the adherend, the thin film sheet 2 is likely to peel off from the porous film 1 when a layer of water exists between the thin film sheet 2 and the porous film 1. Therefore, if necessary, the adherend or the thin film sheet 2 may be further sprayed with water using a sprayer or the like to make the thin film sheet 2 easier to peel off from the porous film 1.

(Cosmetic Set)

The present embodiment also includes a cosmetic set including the cosmetic laminate sheet described above and a container for housing the cosmetic laminate sheet.

The shape of the container for housing the laminate sheet is not particularly limited as long as it can house the laminate sheet, and for example, a box-shaped or bag-shaped container can be used. For example, it is possible to use a box having the shape of a general so-called cosmetic compact when the laminate sheet is of a small size, or the container may be a sheet-like bag capable of housing the laminate sheet in a case where the laminate sheet is a tear-off patch type large sheet.

The container preferably exhibits light shielding properties. Exhibiting light shielding properties means having a transmittance of less than 80% for light having a wavelength of 300 nm. The thin film sheet can be protected from light, particularly ultraviolet light as the container for housing the laminate sheet exhibits light shielding properties in this manner.

A desiccant is preferably further enclosed in the container. The cosmetic laminate sheet can be thus maintained and stored in a dry state (a state in which an aqueous liquid is not contained) until immediately before use, and is thus excellent in handleability.

As the desiccant that can be used in the present embodiment, any desiccant that is used in the field of cosmetics can be used without particular limitation, but specific examples thereof include silica gel, calcium oxide, calcium chloride, clay-based desiccants, and synthetic zeolite.

The cosmetic set including the cosmetic laminate sheet of the present embodiment is greatly useful for industrial use since the handleability is excellent, the operation of transferring the laminate sheet to the skin is relatively easy, and the laminate sheet can be accurately attached to the desired adherend (desired place on the skin).

Hereinafter, the present invention will be described more specifically with reference to Examples, but the scope of the present invention is not limited to these.

EXAMPLES (Porous Film)

For Examples, single layer porous films 1 to 3 formed of PET (polyethylene terephthalate) films (contact angle with water:50°), which had a porosity as shown in Table 1 below, was subjected to hydrophilization treatment, and had a thickness of 50 μm, were prepared. A PET film, which was subjected to hydrophilization treatment and had a thickness of 50 μm, an adhesive layer (waterproof silicone adhesive) having a thickness of 23 μm, and a PET film (contact angle with water: 50°) having a thickness of 38 μm were laminated to prepare multilayer porous films 4 to 8 having a porosity shown in Table 1.

The porosity of these porous films 1 to 8 is the porosity A determined by Equation (1).

Examples 1 to 8

Laminate sheets 1 to 8 were fabricated by laminating a polylactic acid thin film sheet (thickness: 500 nm) having a 1 μm colored layer formed by inkjet printing on the porous films 1 to 8 obtained above, respectively.

Comparative Examples 1 to 6

For Comparative Examples, in each case of single layer films and multilayer films, a hydrophilic film having no micropores (porosity: 0%), a hydrophilic film having a porosity A of 5%, and a hydrophilic film having a porosity A of 95% were prepared.

Laminate sheets were fabricated by laminating the same thin film sheet as in Examples on the films.

(Evaluation Test)

The laminate sheets obtained in Examples and Comparative Examples were attached to an adherend, and the attaching properties at that time were evaluated.

First, each laminate sheet was sprayed with water using a sprayer, and then attached so that the thin film sheet was in contact with the adherend. After that, the porous film and the film were peeled off, and the attaching properties were evaluated based on the following criteria.

A: Thin film sheet easily transfers to skin from porous film or film

B: Thin film sheet adheres to part of porous film or film and it is difficult to peel off thin film sheet from porous film or film in some cases.

C: Thin film sheet is not peeled off from porous film or film and it is impossible to transfer thin film sheet to skin The results are summarized in Table 1.

TABLE 1

|  | Example 1 | Example 2 | Example 3 | Example 4 | Example 5 | Example 6 | Example 7 | Example 8 |
|---|---|---|---|---|---|---|---|---|
| Porous film | Single layer | Single layer | Single layer | Multilayer | Multilayer | Multilayer | Multilayer | Multilayer |
| Porosity (%) | 35 | 40 | 50 | 35 | 41 | 46 | 50 | 55 |
| Attaching properties | A | A | A | A | A | A | A | A |

|  |  | Comparative Example 1 | Comparative Example 2 | Comparative Example 3 | Comparative Example 4 | Comparative Example 5 | Comparative Example 6 |
|---|---|---|---|---|---|---|---|
|  | Porous film | Single layer | Single layer | Single layer | Multilayer | Multilayer | Multilayer |
|  | Porosity (%) | 0 | 5 | 95 | 0 | 5 | 95 |
|  | Attaching properties | C | B | B | C | B | B |

<Discussion>

As is clear from the results in Table 1, all of the laminate sheets for cosmetic of the present embodiment were excellent in attaching properties to the adherend. It was also possible to easily perform the attaching operation. On the other hand, in Comparative Examples 1, 2, 4, and 5, the contact area between the laminate sheet and the porous film or film was large, and at the time of attachment, the laminate sheet remained in close contact with the porous film or film side and it was difficult to transfer the laminate sheet to the skin. In Comparative Examples 3 and 6, it was found that the percentage of voids of the porous film was large, the smoothness was impaired, the laminate sheet was caught on the porous surface, and at the time of attachment, the laminate sheet remained in close contact with the porous film or film side and it was difficult to transfer the laminate sheet to the skin.

This application is based on Japanese Patent Application No. 2020-201598 filed on Dec. 4, 2020, the contents of which are included in the present application.

In order to express the present invention, the present invention is described above appropriately and sufficiently through the embodiments with reference to specific examples, drawings and the like. However, it should be recognized by those skilled in the art that changes and/or improvements of the above-described embodiments can be readily made. Accordingly, changes or improvements made by those skilled in the art shall be construed as being included in the scope of the claims unless otherwise the changes or improvements are at the level which departs from the scope of the appended claims.

INDUSTRIAL APPLICABILITY

The present invention has a wide range of industrial applicability in the technical field relating to cosmetics and beauty.

The invention claimed is:

1. A cosmetic laminate sheet comprising:
a porous film having micropores; and
a thin film sheet superposed on the porous film,
wherein the porous film has a porosity of 35% or more and 55% or less.

2. The cosmetic laminate sheet according to claim 1, wherein the porous film is hydrophilic.

3. The cosmetic laminate sheet according to claim 1, wherein the porous film has a portion where the thin film sheet is not laminated.

4. The cosmetic laminate sheet according to claim 1, wherein the porous film has an Asker C hardness of 4 degrees or more and 20 degrees or less.

5. The cosmetic laminate sheet according to claim 1, wherein the porous film has a transmittance of 40% or more for light having a wavelength of 550 nm.

6. The cosmetic laminate sheet according to claim 1, wherein the porous film has an elastic modulus of 100 MPa or more and 100,000 MPa or less.

7. The cosmetic laminate sheet according to claim 1, wherein the thin film sheet has a thickness of 10 nm or more and 10 μm or less.

8. The cosmetic laminate sheet according to claim 1, wherein the thin film sheet is hydrophilic.

9. The cosmetic laminate sheet according to claim 1, wherein the thin film sheet has, on a surface of a porous film side, at least one layer selected from a colored layer, a light scattering layer, and a layer containing a cosmetic ingredient.

10. The cosmetic laminate sheet according to claim 1, further comprising a covering sheet,
wherein the porous film, the thin film sheet and the covering sheet are laminated in this order.

11. A cosmetic set comprising:
the cosmetic laminate sheet according to claim 1; and
a container for housing the cosmetic laminate sheet.

12. The cosmetic set according to claim 11, wherein the container has a transmittance of less than 80% for light having a wavelength of 300 nm.

13. The cosmetic set according to claim 11, wherein a desiccant is further enclosed in the container.

14. The cosmetic laminate sheet according to claim 1, wherein the porosity is defined by the following equation:

$$A = 78.5 \times D^2/P^2,$$

wherein A denotes the porosity, D denotes a diameter of the micropores, and P denotes a pitch between micropores.

* * * * *